US012582621B2

(12) United States Patent
Mansour et al.

(10) Patent No.: US 12,582,621 B2
(45) Date of Patent: Mar. 24, 2026

(54) COMPOSITIONS AND METHODS FOR DELIVERING PHARMACEUTICAL AGENTS

(71) Applicant: Arizona Board of Regents on Behalf of the University of Arizona, Tucson, AZ (US)

(72) Inventors: Heidi M. Mansour, Tucson, AZ (US); Rick G. Schnellmann, Tucson, AZ (US); David Encinas, Tucson, AZ (US)

(73) Assignee: Arizona Board of Regents on Behalf of the Universityof Arizona, Tucson, AZ (US)

( * ) Notice: Subject to any disclaimer, the term of this patent is extended or adjusted under 35 U.S.C. 154(b) by 506 days.

(21) Appl. No.: 18/009,450

(22) PCT Filed: Jun. 11, 2021

(86) PCT No.: PCT/US2021/036980
§ 371 (c)(1),
(2) Date: Dec. 9, 2022

(87) PCT Pub. No.: WO2021/252879
PCT Pub. Date: Dec. 16, 2021

(65) Prior Publication Data

US 2023/0225998 A1 Jul. 20, 2023

Related U.S. Application Data

(60) Provisional application No. 63/037,698, filed on Jun. 11, 2020.

(51) Int. Cl.

| | |
|---|---|
| *A61K 31/185* | (2006.01) |
| *A61K 9/00* | (2006.01) |
| *A61K 9/48* | (2006.01) |
| *A61K 47/36* | (2006.01) |
| *A61P 17/02* | (2006.01) |

(52) U.S. Cl.
CPC .......... *A61K 31/185* (2013.01); *A61K 9/0014* (2013.01); *A61K 9/4816* (2013.01); *A61K 47/36* (2013.01); *A61P 17/02* (2018.01)

(58) Field of Classification Search
CPC .. A61K 31/122; A61K 9/4816; A61K 31/722; A61K 9/0014; A61K 31/185
See application file for complete search history.

(56) References Cited

U.S. PATENT DOCUMENTS

| | | | | |
|---|---|---|---|---|
| 2006/0002974 A1 | 1/2006 | Pacetti et al. | | |
| 2007/0191937 A1* | 8/2007 | Hossainy | A61F 2/91 623/1.42 | |
| 2011/0125287 A1 | 5/2011 | Hotter et al. | | |
| 2017/0360912 A1* | 12/2017 | Lerouge | A61K 47/36 | |

FOREIGN PATENT DOCUMENTS

| | | | |
|---|---|---|---|
| CN | 106344496 A * | 1/2017 | A61K 31/167 |
| WO | WO 2010/009335 | 1/2010 | |
| WO | WO 2016/036823 | 3/2016 | |
| WO | WO-2016036823 A2 * | 3/2016 | A61K 31/185 |
| WO | WO-2019084290 A1 * | 5/2019 | A61K 31/185 |

OTHER PUBLICATIONS

Fattahpour et al (International Journal of Biological Macromolecules, Feb. 2020, vol. 151, pp. 220-229) (Year: 2020).*
Wahba (Biotechnology Progress, Mar./Apr. 2018, vol. 34, pp. 347-361) (Year: 2018).*
Patenall et al (International Journal of Molecular Sciences, 2024, vol. 25, pp. 1-18) (Year: 2024).*
Sklar et al (The Journal of Urology, 1993, vol. 150, pp. 1526-1532) (Year: 1993).*
CN-106344496-A (Google English translation, downloaded Apr. 2025) (Year: 2025).*
Bartkowiak et al., Surface properties and morphology of selected polymers and their blends designed to mucoadhesive dosage forms, Reactive and Functional Polymers, 118: Oct. 19, 2017.
Brako et al., Mucoadhesion of Progesterone-Loaded Drug Delivery Nanofiber Constructs, ACS applied materials & interfaces, 10(16):13381-13389 2018.
Chai, Q. Hydrogels for Biomedical Applications: Their Characteristics and the Mechanisms behind Them, Gels 2017, 3, 6, pp. 1-15.
Dupre, et al., Suramin protects from cisplatin-induced acute kidney injury, Am. J. Physiol. Renal Physiol. Feb. 2016. 1; 310(3):F248-58.
International Search Report & Written Opinion, International Patent Application No. PCT/US2021/036980, mailed Sep. 8, 2021, 9 pages.
Korrapati, et al., Diabetes-Induced Renal Injury in Rats is Attenuated by Suramin, J. Pharmacol. Exp. Ther. Oct. 2012; 343(1):34-43.
Korrapati, et al., Suramin: A Potential Therapy for Diabetic Nephropathy, PLoS One Sep. 2013. 9, 8(9):e73655.
Liu et al., Smart gelation of chitosan solution in the presence of NaHCO3 for injectable drug delivery system, Int J Pharm. Jul. 29, 2011;414(1-2):6-15.

* cited by examiner

*Primary Examiner* — Mark V Stevens
(74) *Attorney, Agent, or Firm* — Casimir Jones, S.C.; Tanya A. Arenson

(57) ABSTRACT

Provided herein are compositions and methods for delivering pharmaceutical agents. In particular, provided herein are hydrogel formulations of suramin for use in wound healing, wound prevention, and other applications.

16 Claims, 19 Drawing Sheets

FIG. 1
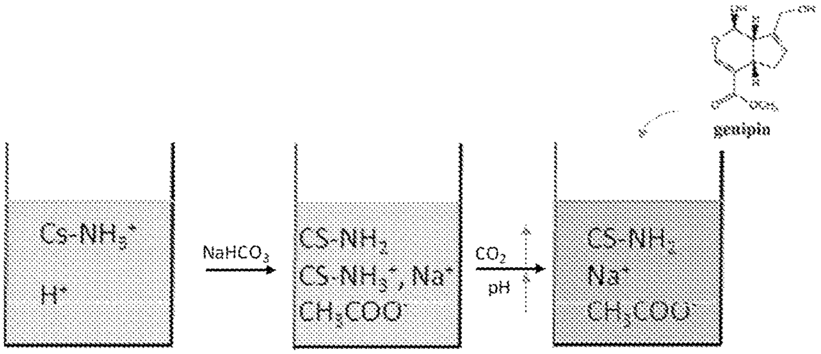
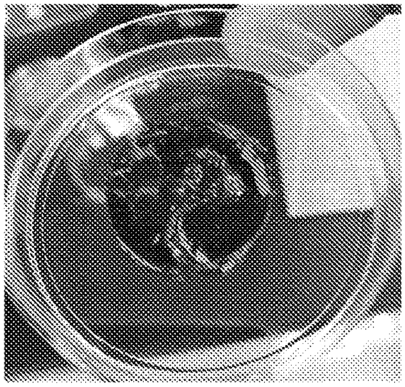
FIG. 2
Optimization of suramin-loaded chitosan hydrogels with different sodium bicarbonate concentrations, n=3
| Con. of NaHCO3 (mol/L) | NaHCO3 (g) | pH | V (mV) |
|---|---|---|---|
| 0 | 0 | 4.46±0.06 | 163.5±2.5 |
| 0.05 | 0.01 | 5.8±0.02 | 88.1±3.1 |
| 0.15 | 0.03 | 6.7±0.02 | 38.4±4.8 |
| 0.2 | 0.05 | 7.02±0.04 | 20.4±3.9 |
Swelling ratio of suramin-loaded chitosan hydrogels with different crosslinking concentrations after 6 h, n=3
| Con. of NaHCO3 (mol/L) | GNP % w/w | Swelling ratio (%) | Suramin loaded ( % w/w) |
|---|---|---|---|
| 0.2 | 1 % | 565 ± 30 | 25 |
| 0.2 | 3 % | 289 ± 28 | 25 |
| 0.2 | 5 % | 40 ± 12 | 25 |

1 % w/w

2% w/w

5% w/w

FIG. 4
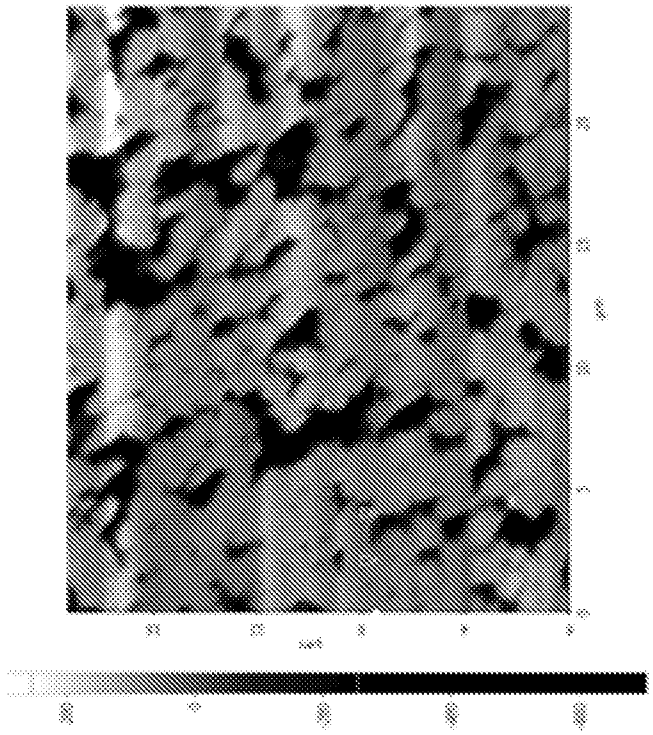
Chitosan 1.5 % Hydrogel (GNP 5 %)
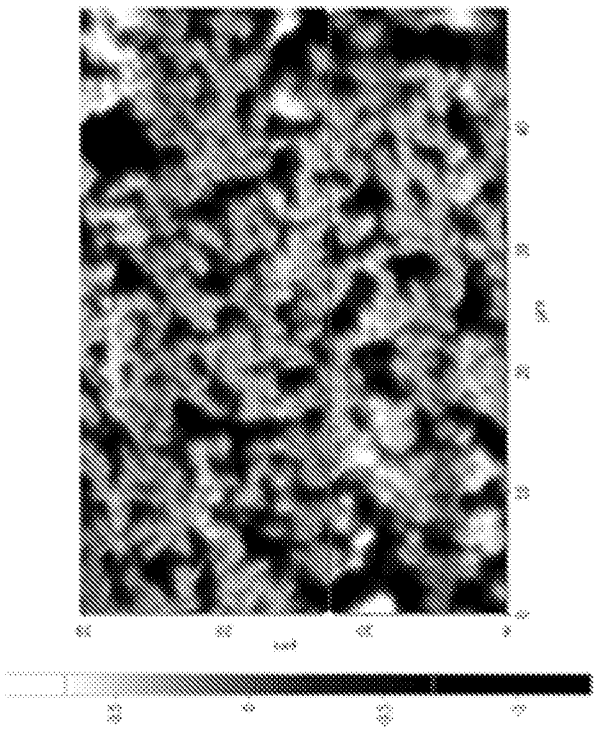
Chitosan 1.5 % Hydrogel (No GNP)
| Formulation | Roughness (nm) | Area (um²) | Pore size (average) |
|---|---|---|---|
| Chitosan 1.5 % Hydrogel (GNP 5 %) | 15223.9 | 118.77 | 1.9 |
| Chitosan 1.5 % Hydrogel (No GNP) | 21.909 | 329.55 | 2.5 |

FIG. 6A-D
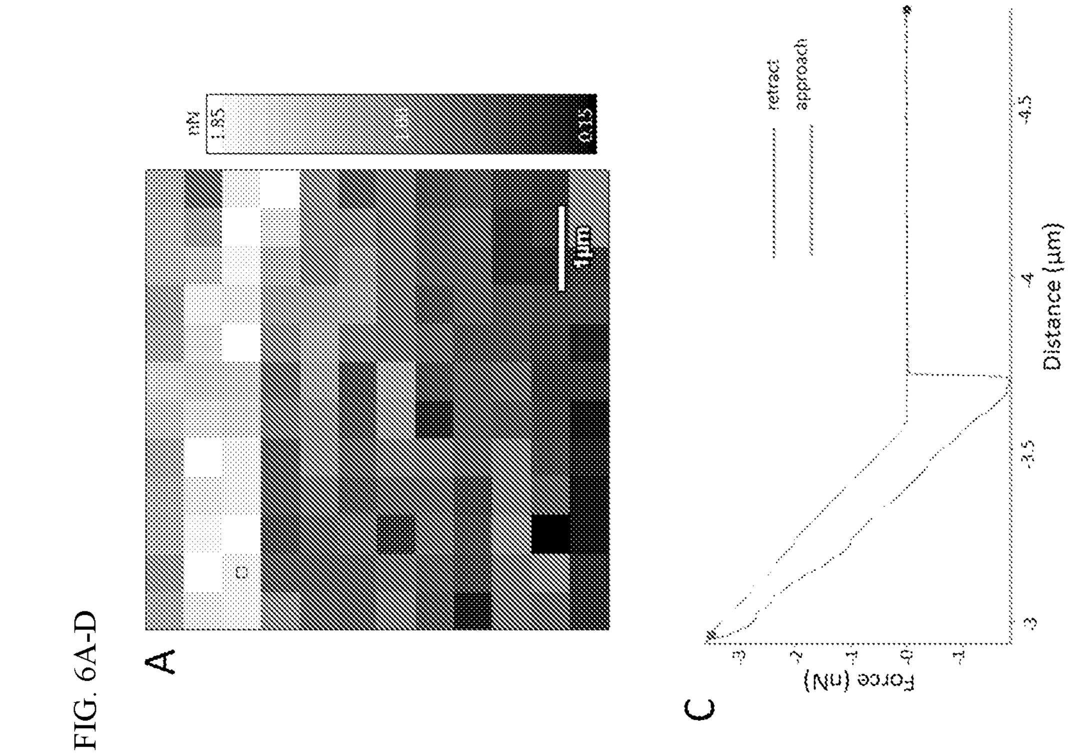
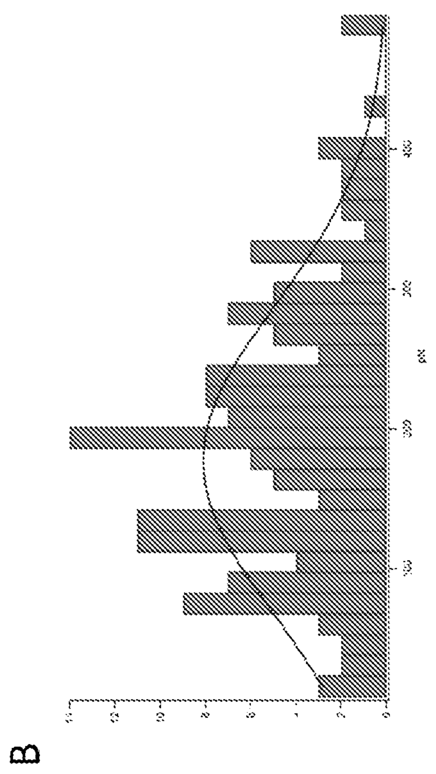
D
| Sample | Hardness (kPa ) | Fmax (nN) | Adhesiveness (pN ± SD) |
|---|---|---|---|
| Chitosan (1 % w/v) | 84.63 ± 15.65 | 4.08 ± 0.95 | 35.95 ± 25.1 |
| Chitosan (1.5% w/v) | 90.50 ± 25.69 | 5.65 ± 1.15 | 139 ± 42 |

FIG. 7A-C
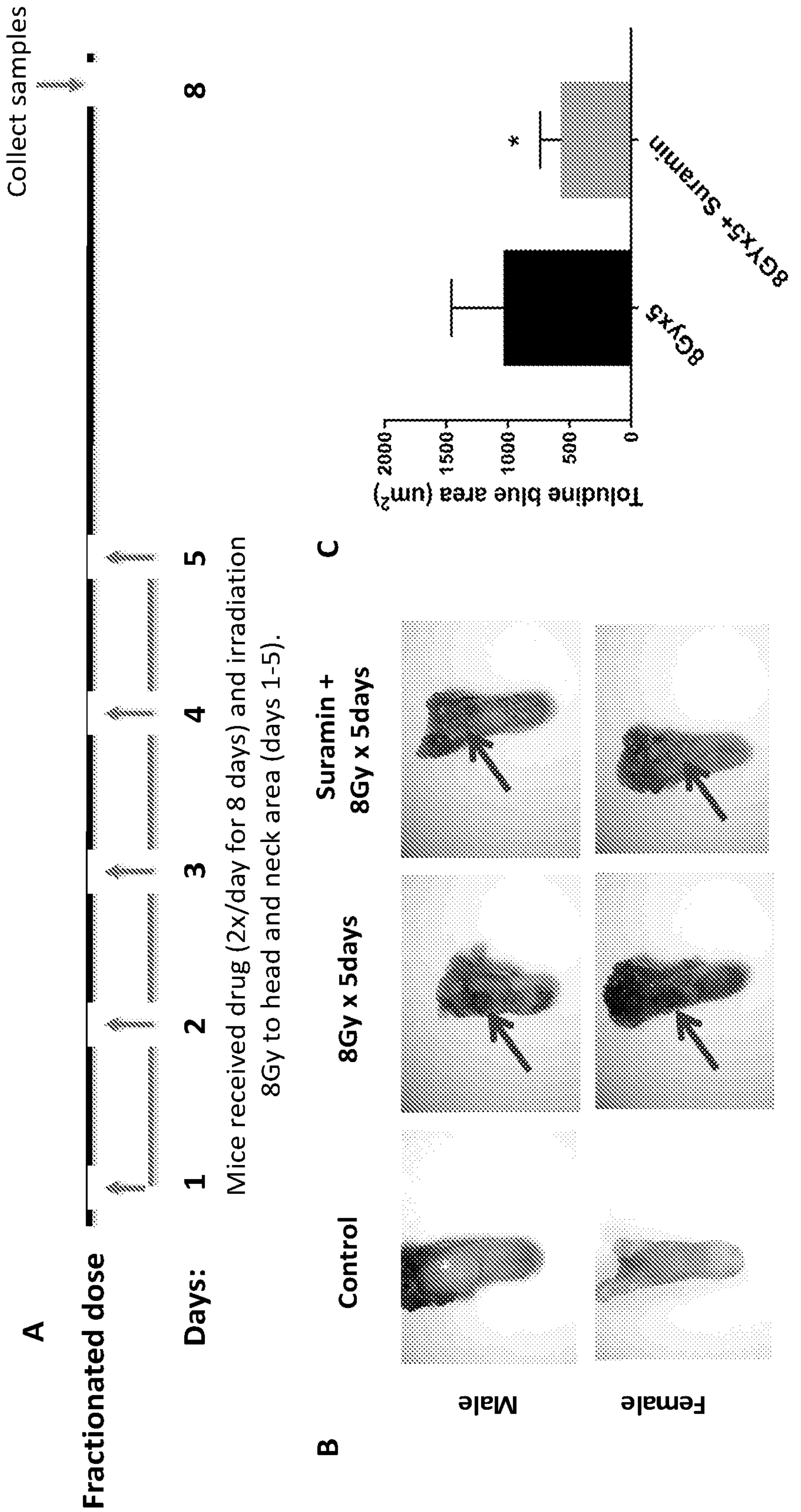
A
Fractionated dose
Collect samples
Days: 1 2 3 4 5 8
Mice received drug (2x/day for 8 days) and irradiation 8Gy to head and neck area (days 1-5).
B
Control     8Gy x 5days     Suramin + 8Gy x 5days
Male
Female
C
Toludine blue area (um$^2$)
*
8Gyx5     8GYx5+ Suramin O-Carboxymethyl chitosan (O-CMC)

Chitosan (CS)

N,O-Carboxymethyl chitosan (N,O-CMC)

N,N-Carboxymethyl chitosan (N,N-CMC)

CMC HD 1 % w/w GNP

CMC HD 3 % w/w GNP

CMC HD 5 % w/w GNP

FIG. 11
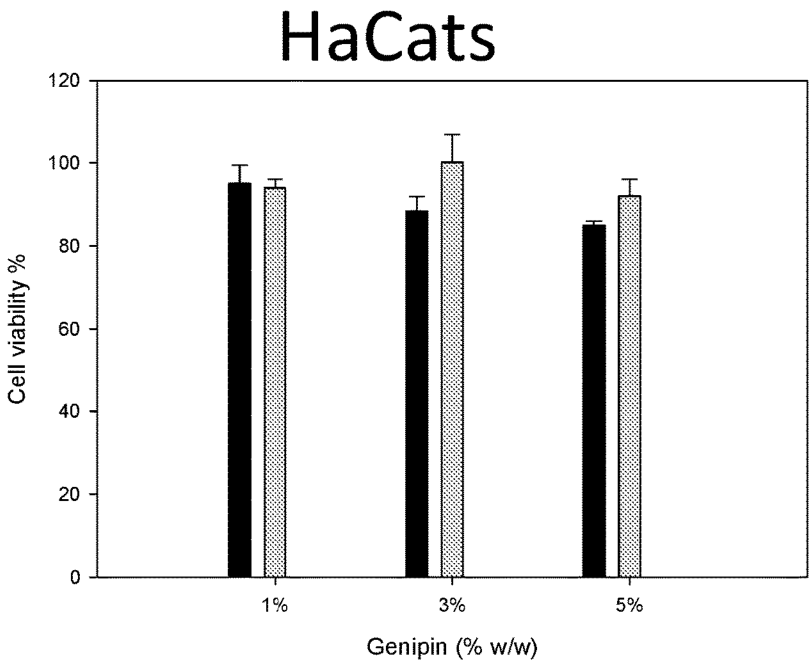
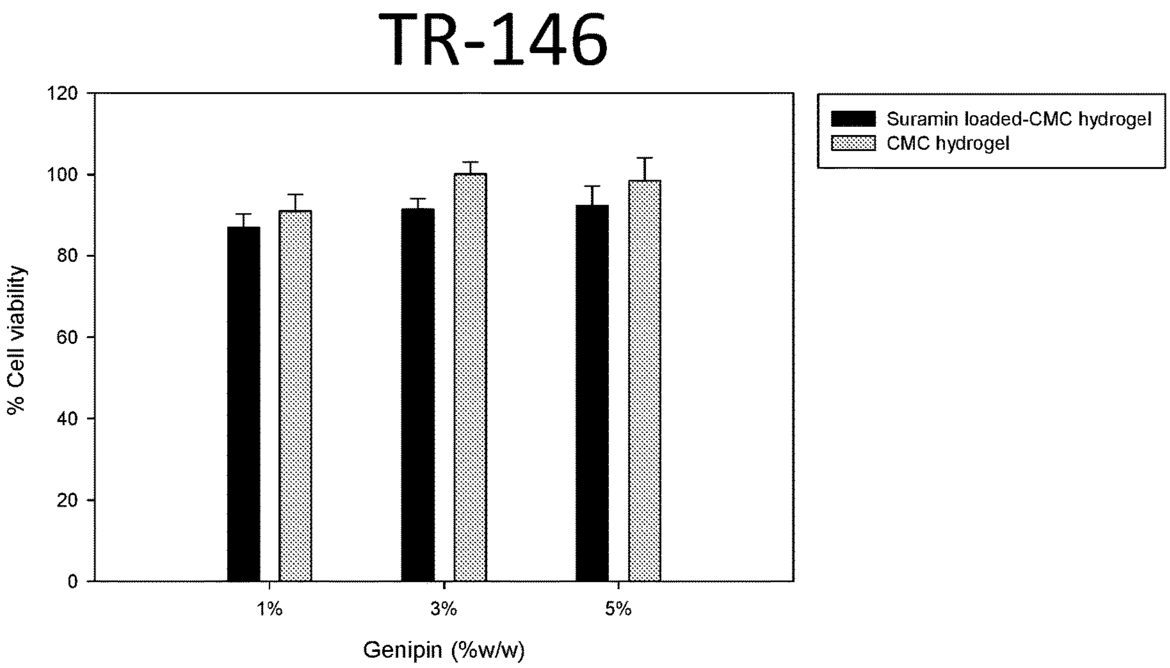

FIG. 12
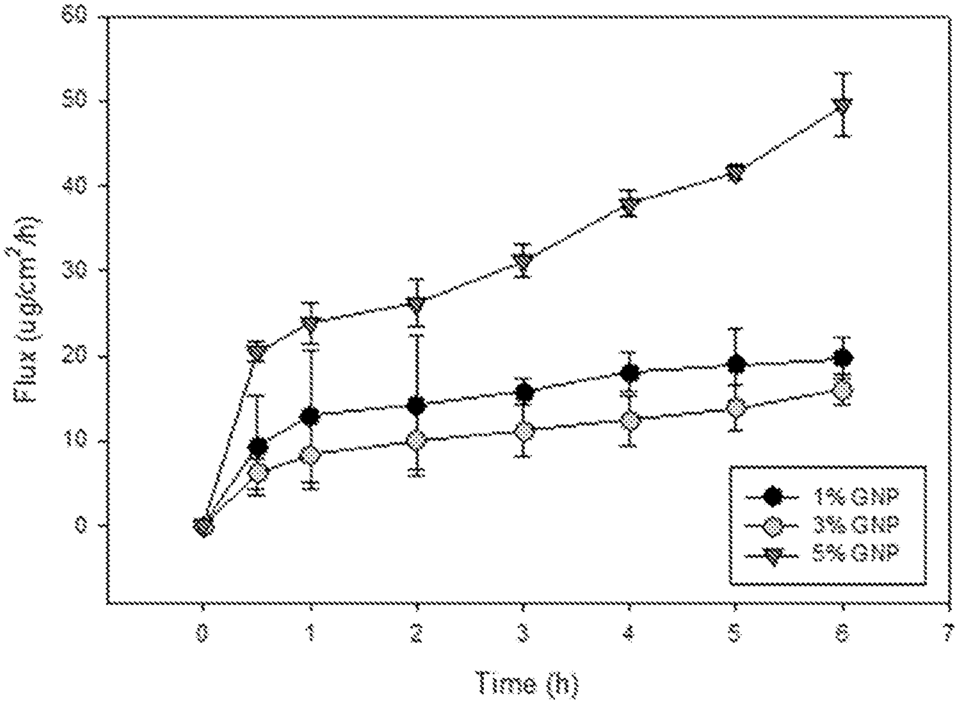
$$Jss = \frac{\Delta Qt}{\Delta t \times S}$$
$$Kp = \frac{Jss}{Cd}$$
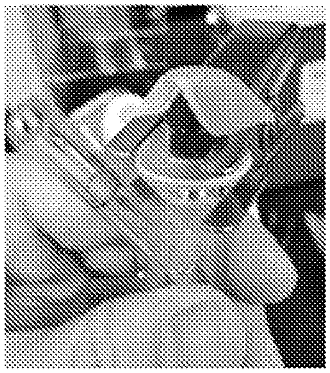
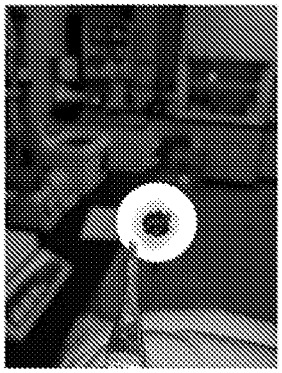
| Sample | Flux (μg/cm²/h) | Permeability coefficient, $k_p$ (cm/h) | Drug retention (ug/cm²) |
|---|---|---|---|
| 1% (w/w) GNP | 1.7 ± 0.21 | $4.4 \times 10^{-3} \pm 4.28 \times 10^{-5}$ | 3.1 ± 0.7 |
| 3% (w/w) GNP | 1.5 ± 0.37 | $3.1 \times 10^{-3} \pm 7.5 \times 10^{-5}$ | 3.4 ± 0.9 |
| 5% (w/w) GNP | 2.81 ± 0.64 | $3.6 \times 10^{-3} \pm 3.2 \times 10^{-4}$ | 8.5 ± 2.3 |

FIG. 13
| Solution | Concentration |
| --- | --- |
| Poloxamer | 20% w/v |
| CMC | 1,3 and 5% (w/w) |
| Suramin | 2 mg/ml |
CMChitosan polymer
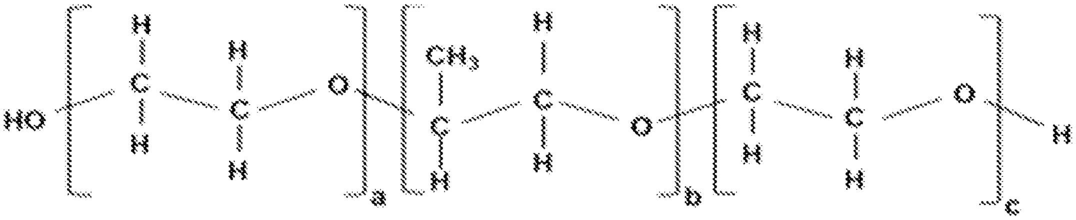
Ethylene oxide block Propylene oxide block Ethylene oxide block
Poloxamer407 polmer
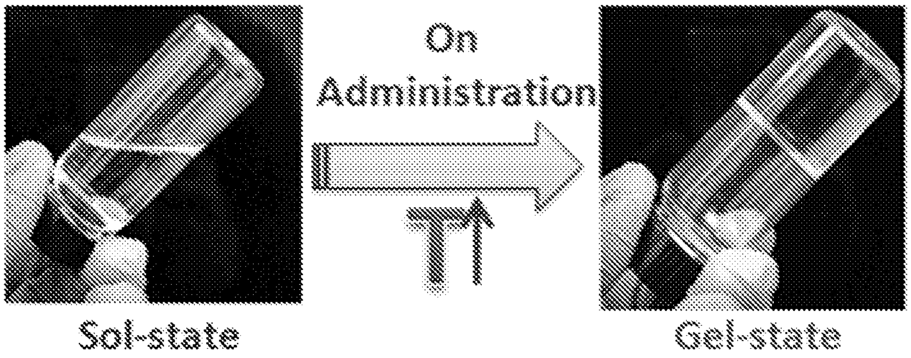

FIG. 14
| Poloxamer 407 (%) | $T_{onset}$ (°C) | cmT (°C) | ΔH (cmT) (J/g) | Transition temperature (°C) |
|---|---|---|---|---|
| 17 | - | - | - | No gelation |
| 18 | 15.16 | 17.85 | 2.5 | 31.5 |
| 19 | 14.58 | 17.28 | 2.56 | 28 |
| 20 | 14.11 | 16.88 | 2.65 | 26 |
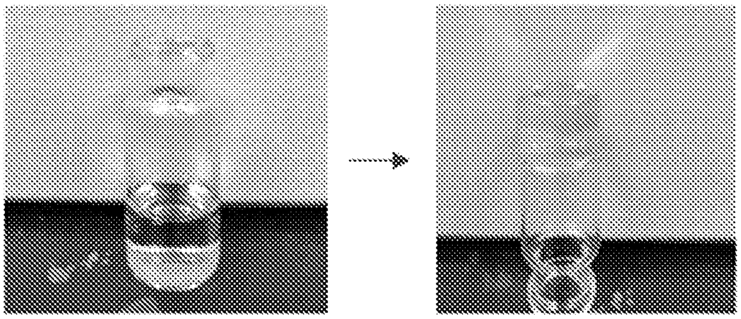
Sol-gel transition of Poloxamer HD at 30 °C
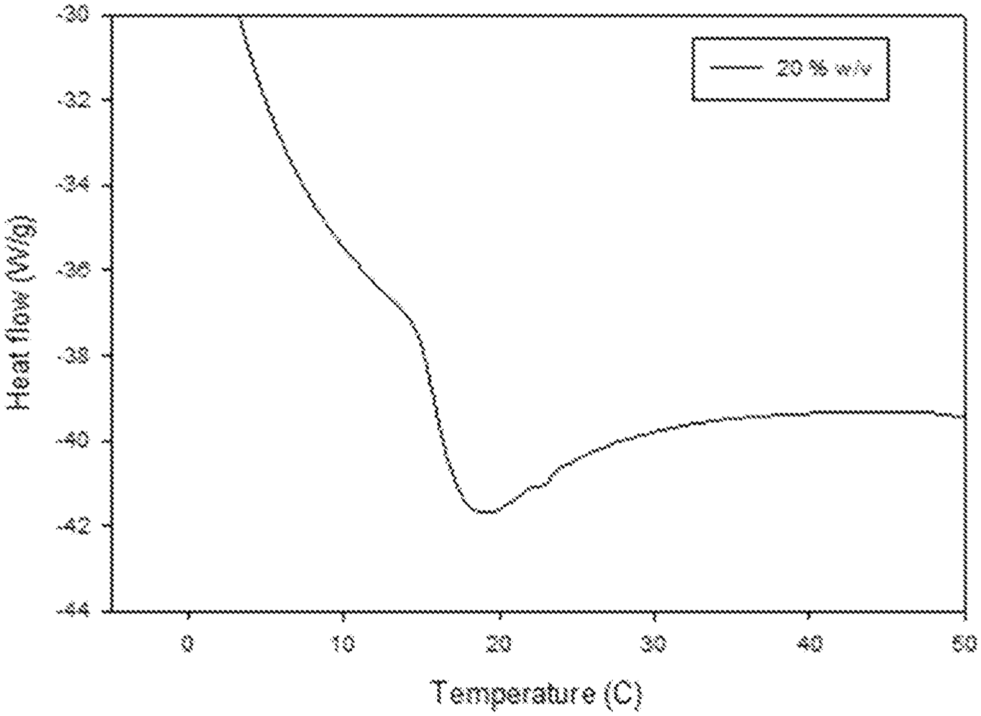
Differential Scanning Calorimetry (DSC) Thermogram of poloxamer solution at rate of 40 °C/min.

| Sample | Flux (μg/cm²/h) | Permeability coefficient, $k_p$ (cm/h) | Drug retention (ug/cm²) |
|---|---|---|---|
| Polox 20 % with 5% (w/w) CMC | 22.02 ± 5.8 | 0.0073±4.28x10⁻² | 27.1 ± 7.1 |
| Polox 20 % | 14.37 ± 2.7 | 0.0064±3.2x10⁻² | 16.9 ± 5.9 |

$$Jss = \frac{\Delta Qt}{\Delta t \times S}$$

$$Kp = \frac{Jss}{Cd}$$

FIG. 19
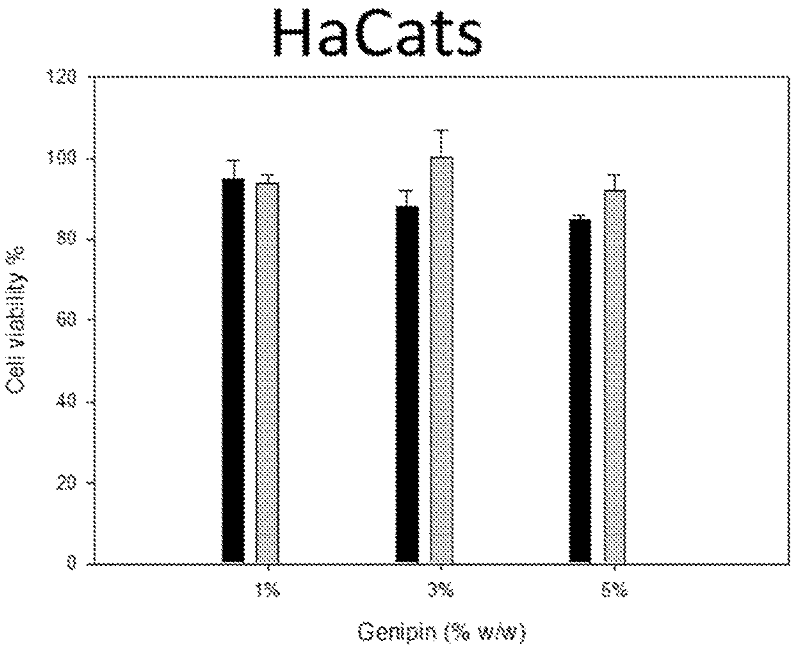
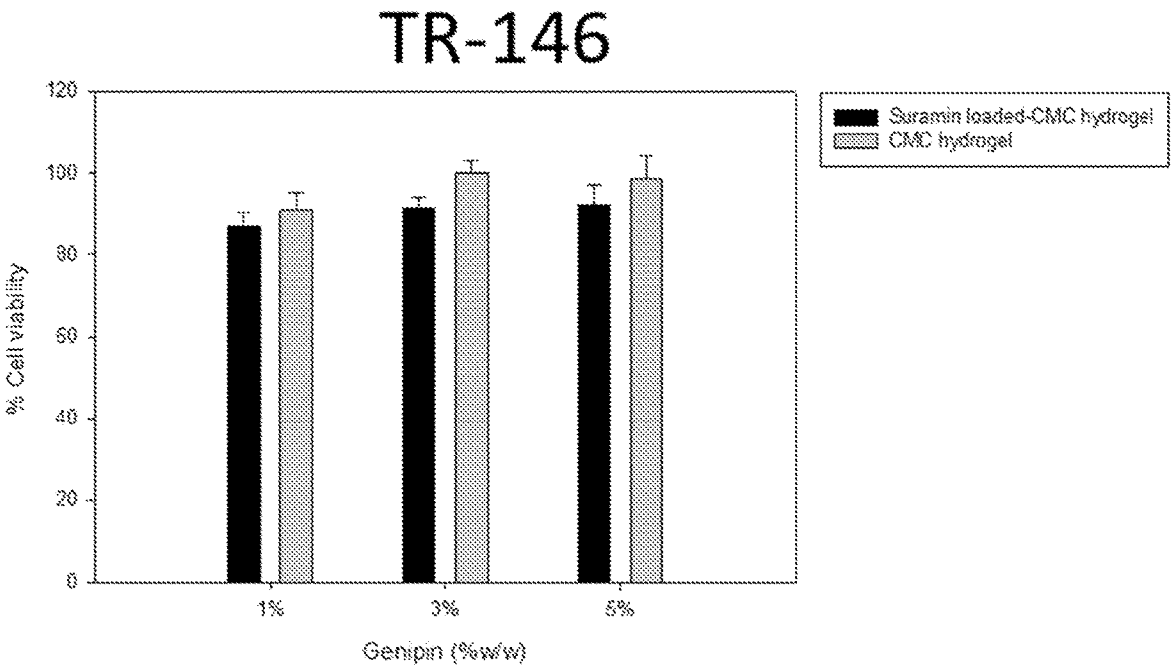

| Sample | Flux (μg/cm²/h) | Drug Retention (ug/cm²) |
|---|---|---|
| Free suramin | 0.42 ± 0.15 | 23.04 ± 5.33 |
| CMC Hydrogel | 0.37 ± 0.04 | 24.06 ± 7.33 |
| Poloxamer Hydrogel | 1.18 ± 0.7 | 16.9 ± 5.9 |
| Molecular Mix Hydrogel (5% CMC) | 2.53 ± 0.27 | 27.1 ± 7.1 |

| Sample | Flux (μg/cm²/h) | Drug Retention (ug/cm²) |
|---|---|---|
| Free suramin | 66.76 ± 3.7 | 57.52 ± 0.38 |
| CMC Hydrogel | 55.08 ± 4.7 | 39.43 ± 1.41 |
| Poloxamer Hydrogel | 31.70 ± 6.7 | 36.69 ± 1.56 |
| Molecular Mix Hydrogel (5% CMC) | 56.01 ± 2.1 | 47.77 ± 0.74 |

COMPOSITIONS AND METHODS FOR DELIVERING PHARMACEUTICAL AGENTS

CROSS-REFERENCE TO RELATED APPLICATIONS

This application is a Section 371 U.S. national stage entry of International Patent Application No. PCT/US2021/036980, International Filing Date Jun. 11, 2021 which claims priority to and the benefit of U.S. Provisional Application No. 63/037,698 filed Jun. 11, 2020, which are hereby incorporated by reference in their entireties.

FIELD

Provided herein are compositions and methods for delivering pharmaceutical agents. In particular, provided herein are hydrogel formulations of suramin for use in wound healing, wound prevention, and other applications.

BACKGROUND

A chronic wound is a wound that does not heal in an orderly set of stages and in a predictable amount of time the way most wounds do; wounds that do not heal within three months are often considered chronic. Chronic wounds are detained in one or more of the phases of wound healing. For example, chronic wounds often remain in the inflammatory stage too long. To overcome that stage and jump-start the healing process a number of factors need to be addressed such as bacterial burden, necrotic tissue, and moisture balance of the whole wound. In acute wounds, there is a precise balance between production and degradation of molecules such as collagen; in chronic wounds this balance is lost and degradation plays a large role.

Chronic wounds may never heal or may take years to do so. These wounds cause patients severe emotional and physical stress and create a significant financial burden on patients and the healthcare system. In addition to poor circulation, neuropathy, and lack of activity (e.g., in bedridden individuals), factors that contribute to chronic wounds include systemic illnesses, age, and repeated trauma. Comorbid ailments that may contribute to the formation of chronic wounds include vasculitis (an inflammation of blood vessels), immune suppression, pyoderma gangrenosum, diabetes, cancer treatments, and diseases that cause ischemia. Immune suppression can be caused by illnesses or medical drugs used over a long period, for example steroids. Emotional stress can also negatively affect the healing of a wound, possibly by raising blood pressure and levels of cortisol, which lowers immunity.

Though treatment of the different chronic wound types varies slightly, appropriate treatment seeks to address the problems at the root of chronic wounds, including ischemia, bacterial load, and imbalance of proteases. Peri wound skin issues should be assessed and their abatement included in a proposed treatment plan. Various methods exist to ameliorate these problems, including antibiotic and antibacterial use, debridement, irrigation, vacuum-assisted closure, warming, oxygenation, moist wound healing, removing mechanical stress, and adding cells or other materials to secrete or enhance levels of healing factors.

Additional treatments for wounds are needed.

SUMMARY

There is a long unmet need for new treatments for wounds, in particular chronic wounds, as well as a large patient population. The present invention meets this need by providing improved formulations of suramin for use in wound healing and prevention in a variety of patient populations.

Experiments conducted during the course of the development of the present invention developed formulations of suramin encapsulated in polymeric (e.g., chitosan) hydrogels that are biocompatible and biodegradable. Synthesis, physiochemical characterization, in vitro sustained drug release, hydrogel swelling, and hydrogel mucoadhesion analysis showed high encapsulation efficiency, high drug loading, and sustained suramin release. Such compositions find use in a variety of applications, including, but not limited to, wound healing.

For example, in some embodiments, provided herein is a composition, comprising: suramin encapsulated in a polymeric hydrogel. The present disclosure is not limited to particular polymers. For example, in some embodiments, the hydrogel comprises one or more polymers selected from, for example, chitosan, carboxymethyl chitosan, N, O-carboxymethyl chitosan, trimethyl chitosan, hydroxypropyltrimethylammonium chloride chitosan, thiolate chitosan, cellulose, methyl cellulose, ethyl cellulose, hydroxymethyl cellulose, sodium alginate, hyaluronic acid, poly (ethylene glycol) (PEG), polyvinylpyrrolidone, dextran, arabic gum. poloxamers, poly(N-isopropyl acrylamide) (PNIPAAm), poly(acrylamide) (PAAm), poly-methacrylic acid (PMAA), poly(acrylic acid) (PAA), poly(N-isopropylacrylamide or a combination thereof. In some embodiments, the polymer is chitosan. In some embodiments, the hydrogel is crosslinked. The present disclosure is not limited to a particular type of crosslinking. For example, in some embodiments, the crosslinking is chemical, physical, or oxidative. For example, in some embodiments, the hydrogel comprises a crosslinker (e.g., including but not limited to, glutaraldehyde, genipin, palladium cation, diisocyanate, or acrylic acid). In some embodiments, the polymer (e.g., chitosan) is crosslinked in the presence of sodium bicarbonate. In some exemplary embodiments, the chitosan is crosslinked with 0 to 1M (e.g., 0.1M to 0.5M (e.g., 0.2 M)) sodium bicarbonate and 0.5% to 5% (e.g., 1% to 3% by weight) genipin (GNP). In some embodiments, the chitosan is at a concentration of 0.5 to 5% w/v (e.g., 1-1.5%) in the hydrogel.

Further embodiments provide a method of treating wounds in a subject, comprising: administering the compositions described herein to a subject with a wound under conditions such that the wound heals.

Additional embodiments provide a method of preventing a wound, comprising: administering a composition described herein to a subject at risk of developing a wound under conditions such that formation of the wound is prevented. In some embodiments, the composition is administered prior to radiation therapy (e.g., radiation therapy of mouth and/or neck). In some embodiments, the administering prevents formation of oral mucositis in the subject.

In some embodiments, the wound is an acute wound or a chronic wound or ulcer. In some embodiments, the subject has diabetes or mucositis (e.g., induced by cancer treatment such as radiation). In some embodiments, the method further comprises administering an additional treatment for the wound (e.g., an antibiotic or a pain reliever (e.g., non-steroidal anti-inflammatory agent)).

Yet other embodiments provide the use of the compositions described herein to treat, prevent, or heal a wound in a subject.

Certain embodiments provide the compositions described herein for use in treating or preventing a wound.

Additional embodiments are described herein.

DESCRIPTION OF THE FIGURES

FIG. 1 shows methodology for generating chitosan hydrogels with solvent casting (top) and images of chitosan hydrogels (bottom).

FIG. 2 optimization of chitosan hydrogels.

FIG. 4 shows AFM characterization of chitosan hydrogels.

FIG. 6A-D shows mechanical properties of chitosan hydrogels.

FIG. 7A-C shows that suramin prevents the deleterious effects of radiation in vivo. A, Fractionated irradiation and drug treatment scheme for mice. B, Representative pictures of Toluidine blue staining in fractionated-dose irradiation experiment indicating a) no irradiation control, b) fraction dose 8 Gy×5, and c) 8 Gy×5+ topical Suramin treatment. Arrows indicate ulcers (mucositis).

FIG. 11 shows cytotoxicity of suramin/carboxylmethyl chitosan hydrogels.

FIG. 12 shows suramin diffusion through Strep-M from suramin/carboxylmethyl chitosan hydrogels.

FIG. 13 shows the structure and images of suramin/carboxylmethyl chitosan/poloxamer hydrogels.

FIG. 14 shows the sol-gel transition and DSC of poloxamer hydrogels.

FIG. 19 shows cytotoxicity of suramin/carboxylmethyl chitosan/poloxamer hydrogels.

DEFINITIONS

Figure 3:
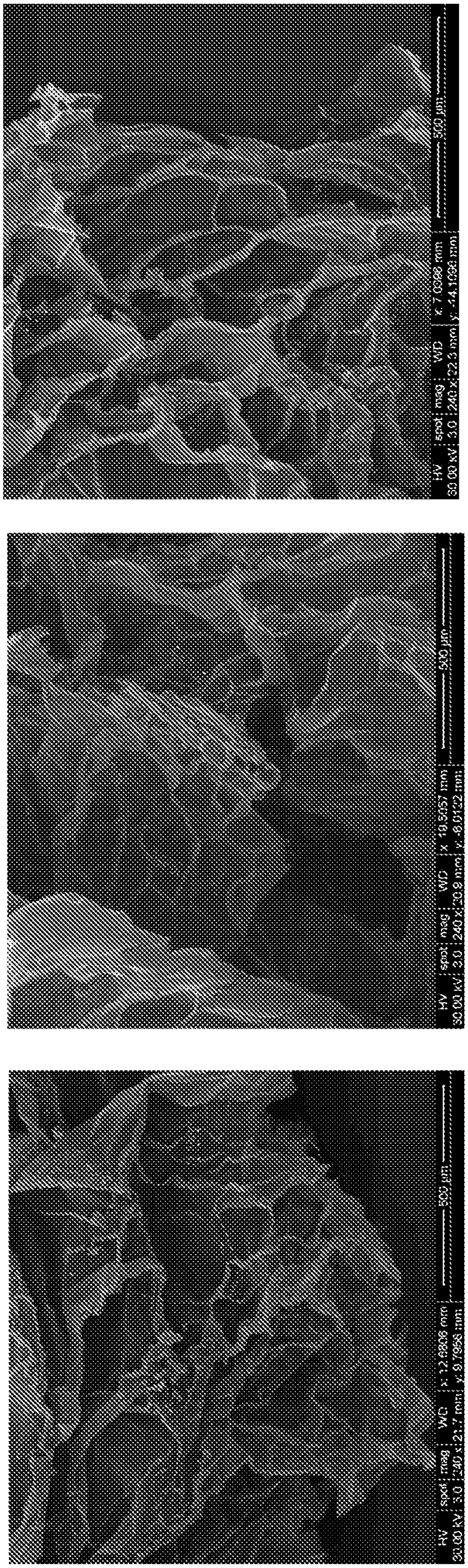
FIG. 3 shows SEM images of chitosan hydrogels with different crosslinker concentration.

As used herein, the term “subject” refers to any animal (e.g., a mammal), including, but not limited to, humans, non-human primates, rodents, and the like, which is to be the recipient of a particular treatment. Typically, the terms “subject” and “patient” are used interchangeably herein in reference to a human or non-human mammal subject.

As used herein, the term “diagnosed,” as used herein, refers to the recognition of a disease by its signs and symptoms (e.g., resistance to conventional therapies), or genetic analysis, pathological analysis, histological analysis, and the like.

As used herein, the term “effective amount” refers to the amount of a compound (e.g., a compound of the present disclosure) sufficient to effect beneficial or desired results. An effective amount can be administered in one or more administrations, applications or dosages and is not limited to a particular formulation or administration route.

As used herein, the term “co-administration” refers to the administration of at least two agent(s) (e.g., a compound of the present disclosure) and one or more additional agents or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term “pharmaceutical composition” refers to the combination of an active agent with a carrier, inert or active, making the composition especially suitable for diagnostic or therapeutic use in vivo, in vivo or ex vivo.

As used herein, the term “pharmaceutically acceptable carrier” refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington’s Pharmaceutical Sciences, 15th Ed., Mack Publ. Co., Easton, PA, (1975)).

As used herein, the term “sample” is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present disclosure.

As used herein, the terms “purified” or “to purify” refer, to the removal of undesired components from a sample. As used herein, the term “substantially purified” refers to molecules that are at least 60% free, at least 65% free, at least 70% free, at least 75% free, at least 80% free, at least 85% free, at least 90% free, at least 95% free, at least 96% free, at least 97% free, at least 98% free, at least 99% free, or 100% free from other components with which they usually associated.

As used herein, the term “modulate” refers to the activity of a compound (e.g., a compound of the present disclosure) to affect (e.g., to promote or retard) an aspect of cellular function.

As used herein, the phrase “in need thereof” means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, condition, or injury is prevalent.

DETAILED DESCRIPTION

Suramin has a long historical precedence of safety in humans spanning 100 years (see, e.g., Korrapati, et al., PLoS One 2013 Sep. 9, 8(9):e73655; Korrapati, et al., J. Pharmacol. Exp. Ther. 2012 October; 343(1):34-43; Dupre, et al., Am. J. Physiol. Renal Physiol. 2016 Feb. 1; 310(3):F248-58). Currently, for example, it is approved for African Sleeping Sickness in Germany.

Suramin is a polysulfonated naphthyl-urea:

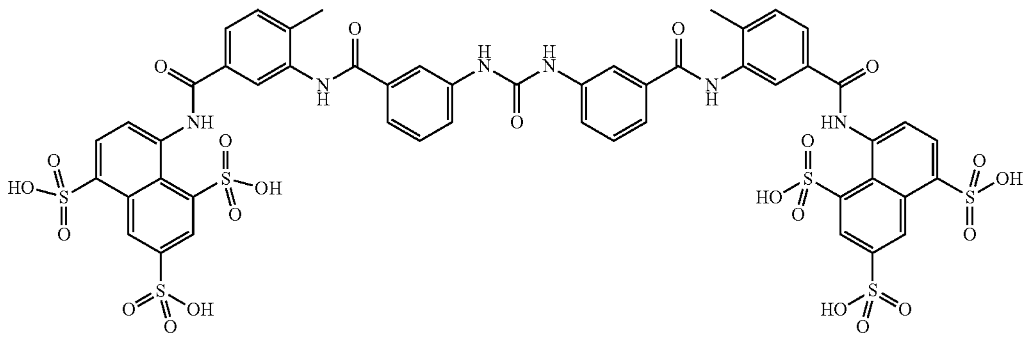 [SMILES: Cc1ccc(C(=O)Nc2ccc(S(=O)(=O)O)c3cc(S(=O)(=O)O)cc(S(=O)(=O)O)c23)cc1NC(=O)c1cccc(NC(=O)Nc2cccc(C(=O)Nc3cc(C(=O)Nc4ccc(S(=O)(=O)O)c5cc(S(=O)(=O)O)cc(S(=O)(=O)O)c45)ccc3C)c2)c1]

Provided herein are new formulations of suramin for use in wound healing (e.g., wound healing in chronic wound injury in mucositis (head/neck cancer therapy-induced), wound prevention (e.g., from radiation therapy) and chronic wound injury in diabetic toot ulcers).

In some embodiments, provided herein are polymeric hydrogel delivery systems for suramin. In some embodiments, hydrogels comprise a material (e.g., polymer) with suitable adhesion, a good swelling ratio that can gives hydrogel hydration with different crosslink density, good stability and sustained release (e.g., when applied to a tissue). In some embodiments, materials also have hydrogen bonding capacity to improve mucoadhesivity; mechanical properties as hardness, cohesiveness, and compressibility; and different polymer charge (anionic, nonionic and cationic).

The present disclosure is not limited to particular polymers. For example, in some embodiments, the hydrogel comprises a polymer selected from, for example, chitosan, carboxymethyl chitosan (CMC), N, O-carboxymethyl chitosan, trimethyl chitosan, hydroxypropyltrimethylammonium chloride chitosan, thiolate chitosan, cellulose, methyl cellulose, ethyl cellulose, hydroxymethyl cellulose, sodium alginate, hyaluronic acid, poly (ethylene glycol) (PEG), polyvinylpyrrolidone, dextran, arabic gum. poloxamers, poly(N-isopropyl acrylamide) (PNIPAAm), poly(acrylamide) (PAAm), poly-methacrylic acid (PMAA), poly(acrylic acid) (PAA), poly(N-isopropylacrylamide or a combination thereof.

In some embodiments, the polymer is chitosan or CMC. In some embodiments, the polymer is a combination of CMC and poloxamer.

In some embodiments, the polymer is a poloxamer. Poloxamers are nonionic triblock copolymers composed of a central hydrophobic chain of polyoxypropylene (poly(propylene oxide)) flanked by two hydrophilic chains of polyoxyethylene (poly(ethylene oxide)).

In some embodiments, cross-linked hydrogels are provided. The present disclosure is not limited to a particular type of crosslinking. For example, in some embodiments, the crosslinking is chemical, physical, or oxidative.

In polymer chemistry, when a polymer is said to be "cross-linked", it usually means that the entire bulk of the polymer has been exposed to the cross-linking method. The resulting modification of mechanical properties depends strongly on the cross-link density. Low cross-link densities increase the viscosities of polymer melts. Intermediate cross-link densities transform gummy polymers into materials that have elastomeric properties and potentially high strengths. Very high cross-link densities can cause materials to become very rigid or glassy.

Cross-links can be formed by chemical reactions that are initiated by heat, pressure, change in pH, or irradiation. For example, mixing of an unpolymerized or partially polymerized resin with specific chemicals called crosslinking reagents results in a chemical reaction that forms cross-links. Cross-linking can also be induced in materials that are normally thermoplastic through exposure to a radiation source, such as electron beam exposure, gamma radiation, or UV light.

The present disclosure is not limited to particular chemical crosslinkers. For example, in some embodiments, the crosslinker is glutaraldehyde, genipin, palladium cation, diisocyanate, or acrylic acid.

Where chemical cross-links are covalent bonds, physical cross-links are formed by weak interactions. For example, sodium alginate gels upon exposure to calcium ion, which allows it to form ionic bonds that bridge between alginate chains. Polyvinyl alcohol gels upon the addition of borax through hydrogen bonding between boric acid and the polymer's alcohol groups. Other examples of materials that form physically cross-linked gels include gelatin, collagen, agarose, and agar agar.

Many polymers undergo oxidative cross-linking, typically when exposed to atmospheric oxygen. In some embodiments, an oxidizer such as hydrogen peroxide is used to speed up the process.

In some embodiments, hydrogel preparation is by solvent casting, direct milling, using ionizing radiation to generate main-chain free radicals (e.g., UV irradiation), physical interactions such as entanglements and electrostatics, condensation reactions (e.g., —OH groups or $—NH_2$ with —COOH or derivatives) and cross-linking by free radical polymerization.

In some embodiments, cross-linking utilizes sodium bicarbonate (See e.g., Liu et al., Int J Pharm. 2011 Jul. 29; 414(1-2):6-15; herein incorporated by reference in its entirety).

In some exemplary, non-limiting embodiments, provided herein is a composition, comprising: suramin encapsulated in a hydrogel (e.g., chitosan hydrogel). In some embodiments, the chitosan is crosslinked in the presence of sodium bicarbonate. In some exemplary embodiments, the chitosan is crosslinked with 0 to 1M (e.g., 0.1M to 0.5M (e.g., 0.2 M)) sodium bicarbonate and 0.5% to 5% (e.g., 1% to 3% by weight) genipin. In some embodiments, the chitosan is at a concentration of 0.5 to 5% w/v (e.g., 1-1.5%) in the hydrogel.

Further embodiments provide a method of promoting wound healing comprising administering the suramin compositions described herein to a subject in need thereof.

In some embodiments, the compositions are administered as a pretreatment to prevention formation of a wound (e.g., prior to radiation therapy of the head and/or neck).

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be “acceptable” in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary, shaping the product.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions are constituted from known ingredients in a known manner. This phase typically comprises a lone emulsifier (otherwise known as an emulgent), it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus, creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate. Likewise, those for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Preferred unit dosage formulations are those containing a daily dose or unit, daily subdose, or an appropriate fraction thereof, of an agent. It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In certain embodiments, the present invention provides instructions for administering said wound healing agents (e.g., suramin compositions) to a subject. In certain embodiments, the present invention provides instructions for using the compositions contained in a kit for the treatment of wounds (e.g., providing dosing, route of administration, decision trees for treating physicians for correlating patient-specific characteristics with therapeutic courses of action). In certain embodiments, the present invention provides instructions for using the compositions contained in the kit to treat a variety of medical conditions associated with wounds.

It is contemplated that the agents identified can be administered to subjects or individuals having, susceptible to or at risk of developing chronic wounds and correlated conditions. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is affected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the agents (e.g., suramin) provided herein are administered at about 0.01 mg/kg to about 200 mg/kg, more preferably at about 0.1 mg/kg to about 100 mg/kg, even more preferably at about 0.5 mg/kg to about 50 mg/kg. When the wound healing agents (e.g., suramin) described herein are co-administered with another agent (e.g., as sensitizing agents), the effective amount may be less than when the agent is used alone.

The present invention also includes methods involving co-administration of the agents (e.g., suramin) described herein with one or more additional active agents. Indeed, it is a further aspect of this invention to provide methods for enhancing existing therapies and/or pharmaceutical compositions by co-administering a wound healing agent (e.g., suramin) described herein. In co-administration procedures, the agents may be administered concurrently or sequentially. In one embodiment, the agents (e.g., suramin) described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, in some embodiments, the additional agent is an antibiotic, pain reliever (e.g., NSAID) or other wound healing agent.

In certain embodiments, the present invention provides methods (e.g., therapeutic applications) for treating conditions associated with wounds (e.g., chronic or slow to heal wounds).

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

Example 1

This Example describes generation and testing of suramin-loaded chitosan hydrogels. Hydrogels were crosslinked with genipin in the presence of sodium bicarbonate.

Materials

Chitosan (Low molecular weight), Suramin sodium salt and sodium bicarbonate were purchased from Sigma Aldrich. Genipin was acquire from MedChemexpress Company.

Methods

Preparation of Suramin-Loaded Chitosan Hydrogels

Chitosan solution was prepared by dissolving different amount of chitosan in 1% acetic acid to get 1 and 1.5% w/v concentrations. Before adding Suramin drug, a 0.2 M $NaHCO_3$ solution was added slowly to increase pH to avoid interactions between negatively charged sulfate groups in Suramin and positive $NH_2$ in the polymer chain. Next, 0.1 mL of Suramin solution (20 mg/mL) was added and it was magnetically stirred for 5 min at 500 rpm. After this 1, 3 and 5% w/w of genipin was added at final concentration. Finally, the hydrogel was poured into 24-well plates and cured for 24 h at 30° C. FIG. 1 shows methodology (top) and images (bottom) of chitosan hydrogels.

Results

Results are shown in FIGS. 2-6. Optimization of suramin loaded hydrogels is shown in FIG. 2. Sodium bicarbonate concentrations of 0 to 0.2 M were tested and 0.2 M was selected for further characterization (upper panel of FIG. 2). Genipin concentrations of 1-5% by weight were tested with 0.2 M sodium bicarbonate (lower panel of FIG. 2). FIG. 3 shows SEM images of hydrogels crosslinked with 1.5% genipin.

Thirty Force-Distance curves were acquired across different locations on the sample to average the measured mechanical properties using mapping tool and a V-shape tip of SiN3. The approach curves were used to estimate the depth of indentation, stiffness, Fmax and adhesion properties in the hydrogel at an applied force.

Adhesion force was measured manually by measuring the height of the pull off in the force distance curve (FIG. 6). The work done is measured as the area of the adhesion portion of the curve below the 0 nN line (Cappella, 2016 Physical Principles of Force-Distance Curves by Atomic Force Microscopy *Mechanical Properties of Polymers Measured*

*through AFM Force-Distance Curves* (pp. 3-66): Springer). It was observed that 1.5% w/v chitosan resulted in a larger adhesion force compared to the 1% w/v hydrogel. The hardness of a material describes the resistance of its surface to the penetration of a harder indenter (Caron, 2016). However, when the cantilever is much stiffer than the sample surface, the slope of the Force vs Distance curve allows investigation of the elastic properties of the sample as the relative Hardness, as was almost the same to the two different hydrogels and Fmax is a parameter that tell us the max force of adhesion detected.

FIG. 4 shows AFM images taken to see if there are differences between hydrogel chemical crosslinked with genipin and just physical crosslink with sodium bicarbonate. The pore size in the genipin-crosslinked hydrogel is smaller than the 0% GNP; this is logical because genipin starts to crosslink free amine groups in the chitosan chain, making a more compact hydrogel, as well as having an effect on the interfacial roughness between tip and sample and this can be correlated to the adhesion forces between two samples (Bartkowiak et al., Reactive and Functional Polymers, 118: 10-19 2017). The root mean square surface roughness determined (AFM) for hydrogel for the crosslinked hydrogel vs the free-genipin chitosan hydrogel were 121.54 nm and 21.9 nm respectively (Table in FIG. 6). Since the adhesion between two elastic surfaces is generally reduced with increasing the surface roughness (Brako et al., ACS applied materials & interfaces, 10(16): 13381-13389 2018).

Figure 5:
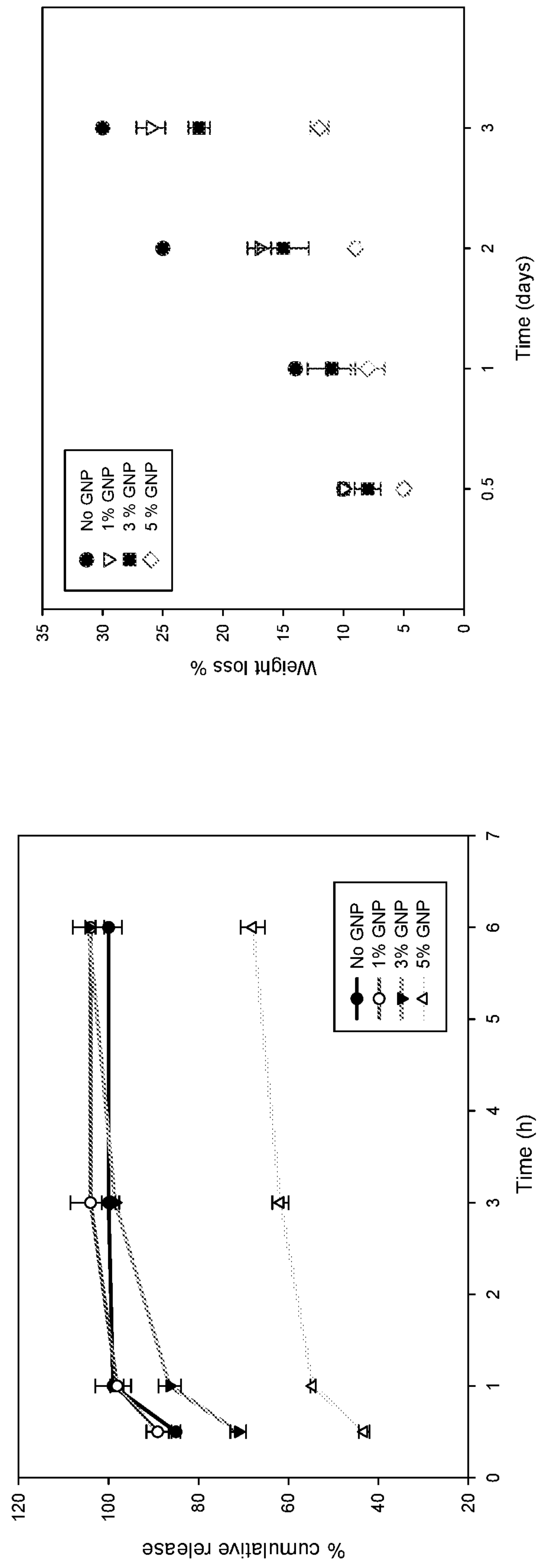
FIG. 5 shows release of suramin (left) and degradation of chitosan hydrogels (right).

FIG. 5 shows a release study of suramin from hydrogels crosslinked using 0-5% genipin (left) and degradation of hydrogels crosslinked using 0-5% genipin (right).

Example 2

This example demonstrates that topical suramin diminishes radiation-induced oral mucosistis.

The head and neck region of six-week-old male and female C57BL/6J mice (4-5 mice/group/sex) were exposed to collimated fractionated radiation (8 Gy on 5 consecutive days). Topically applied suramin (50 mg/ml solution) was applied on day 1 of radiation by intraoral swab and twice daily throughout the experimental period. On day 7, all mice were euthanized and tongues were assessed for development and extent of oral mucositis ulceration on the dorsal surface of the tongue using 1% toluidine blue. Epithelial erosion and ulceration were visible as a deep blue color and ulceration area was measured using NIH Image J software. Histopathological grading (0-4 scale) using an established scale was used to assess OM staging and epithelial thinning.

Results are shown in FIG. 7 and demonstrate that suramin prevents the deleterious effects of radiation in vivo.

Example 3

This example describes additional hydrogels comprising suramin.

Carboxymethyl chitosan (CMC) hydrogels were prepared using the following formulation:

| Solution | Concentration | Volume (ml) |
|---|---|---|
| Genipin | 15 mg/ml | 0.1 |
| CMC | 2% (w/v) | 4 |
| Suramin | 20 mg/ml | 0.1 |

Figure 8A:
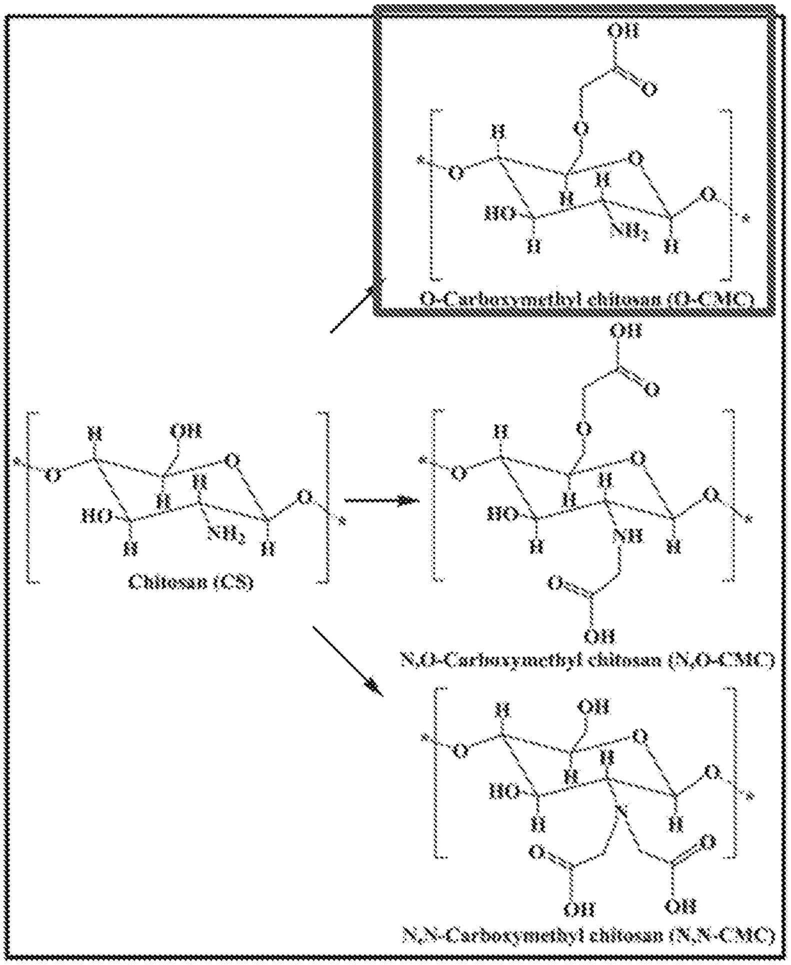
FIG. 8A-B shows the structure and images of suramin/carboxylmethyl chitosan hydrogels.
Figure 8B:
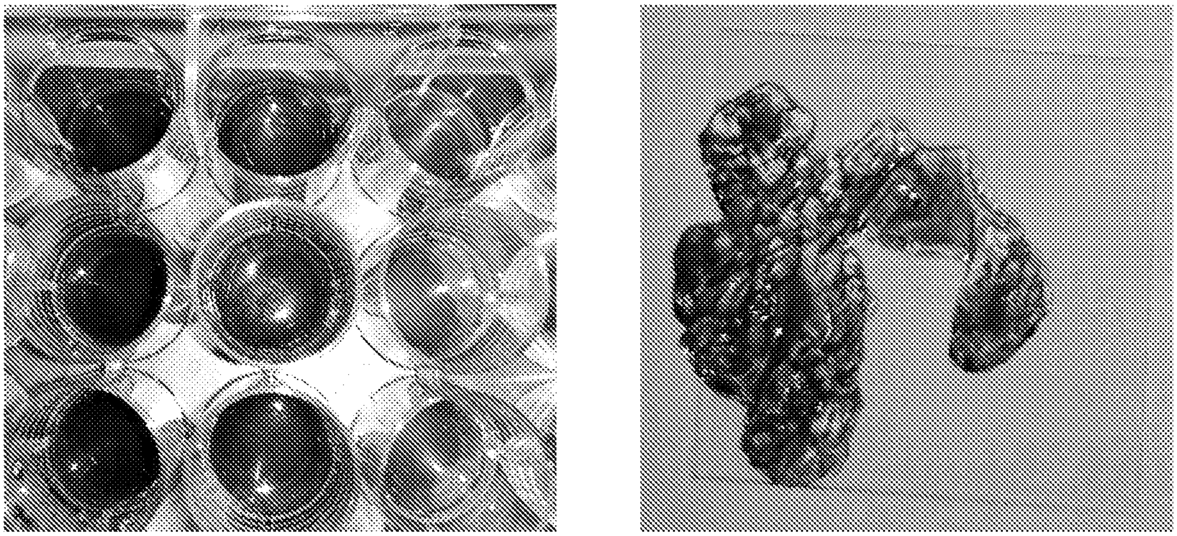
Figure 9:
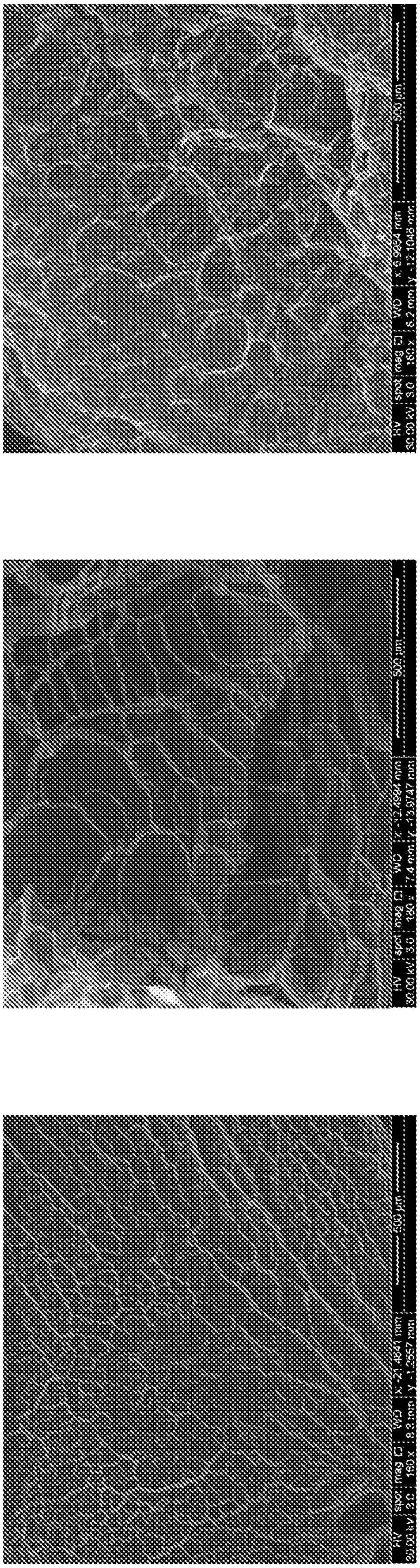
FIG. 9 shows SEM images of suramin/carboxylmethyl chitosan hydrogels.

FIG. 8 shows structure (A) and images (B) of CMC hydrogels crosslinked with genipin. FIG. 9 shows scanning electron micrographs of CMC hydrogels crosslinked with different concentrations of genipin. The below table shows swelling ratio (SR) profile of CMC hydrogels at 37° C. and pH of 7.4. n=3. SR was calculated using the equation SR=(WS−W0)/W0×100%.

| GNP % w/w | Swelling ratio (%) |
|---|---|
| 1% | 205 ± 5 |
| 3% | 63 ± 11 |
| 5% | 41 ± 7 |

Figure 10:
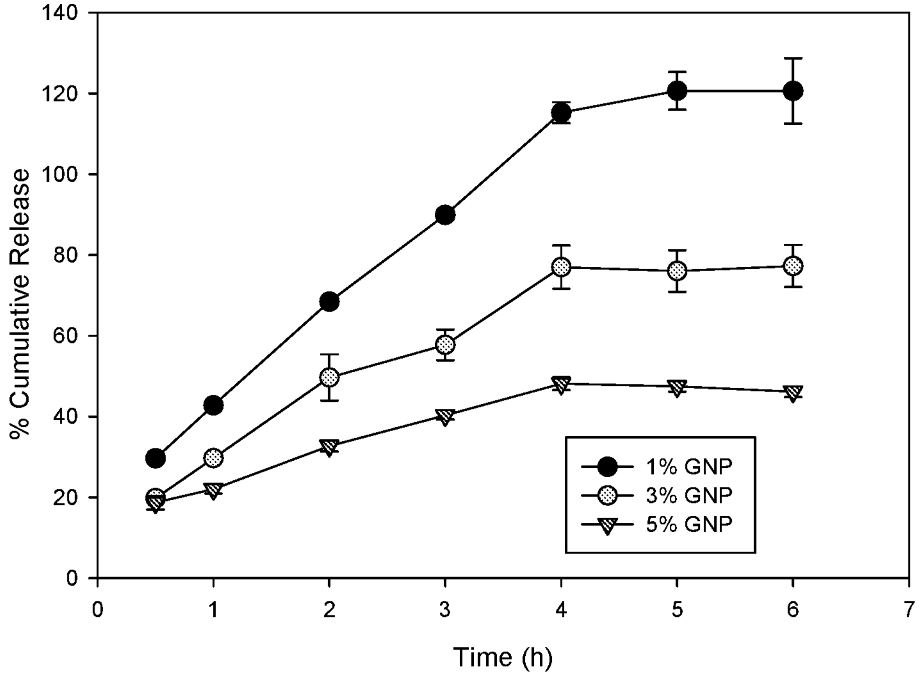
FIG. 10 shows the release profile of suramin from suramin/carboxylmethyl chitosan hydrogels.

FIG. 10 shows the release profile of suramin from CMC hydrogels at 37° C. and a pH of 7.4. 1% GNP-CMC HD showed a release of 100% of the suramin after 3 h.

Cytotoxicity assays were performed by exposing HaCats, a keratinocyte cell line from adult human skin and TR-146, a cell line derived from the neck node of a 67 year-old female (primary tumour was sited in buccal mucosa) to CMC 2%+50, 100 and 200 ul GNP solution (10 mg/ml) and 100 ul suramin solution (10 mg/ml) for 24 hours in a 6-well plate with 100,000 cell per well, seeded for 48 hours. Results are shown in FIG. 11. No toxicity was observed.

Diffusion of suramin hydrogels with different concentrations of genipin through Strep-M was assayed at pH=7.4 and temperature=32° C. Results and experimental details are shown in FIG. 12.

Example 4

This example describes a thermosensitive hydrogel for suramin delivery.

Suramin hydrogels of CMC and poloxamer 407 were prepared as shown in FIG. 13 by dissolving the poloxamer in a suramin-CMC solution.

FIG. 14 shows sol-gel transition and DSC characterization of poloxamer hydrogels. The sol/gel transition has been correlated to intrinsic changes in the micelles properties or to entropic variation in the ordered water molecules close to the PPO segments or to the possibility of formation of a cross-linked and three-dimensional structure able to entrap water in its network. As shown in the Table in FIG. 14, a practically linear correlation was observed between the transition temperature cmT and the concentration of the copolymer. At a high concentration of polymer (>15%, w/v) DSC scans revealed a second peak of small amplitude due to micelle rearrangement, which is the cause of the gel formation. The sol/gel transition temperatures (sgT) as measured by DSC are in a positive agreement with those calculated from the inversion technique shown in the Table in FIG. 14. In addition, the sol/gel transition is not thermodynamically appreciable at Poloxamer 407 concentrations lower than 17.5%, also in this case in agreement with rheological data and does not occur at a low copolymer concentration. Regarding the peak of the sol/gel transition at a Poloxamer 407 concentration ranging between 17.5% and 25% (w/v), a nearly linear correlation exists between the transition temperature sgT and the polymer concentration.

Figure 15:
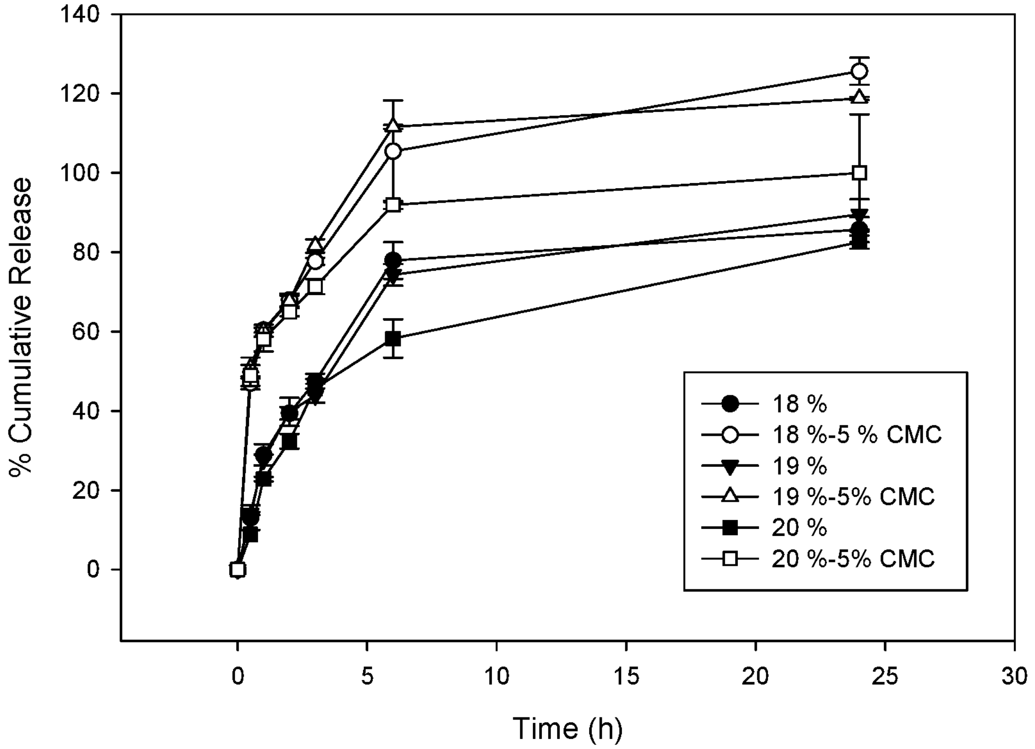
FIG. 15 shows the release profile of suramin from suramin/carboxylmethyl chitosan/poloxamer hydrogels.
Figure 16:
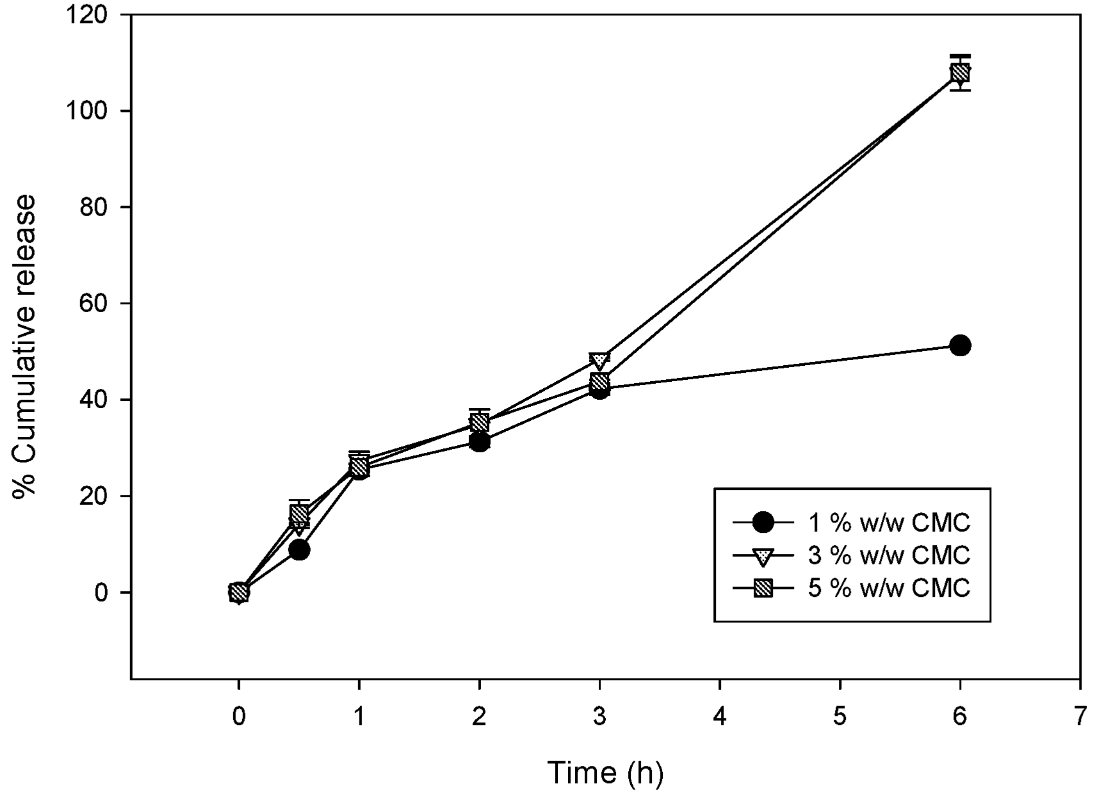
FIG. 16 shows the release profile of suramin from suramin/carboxylmethyl chitosan/poloxamer hydrogels.

FIG. 15 shows a release study of suramin from 5% w/w CMC hydrogels with different concentrations of poloxamer. Solutions were prepared separately, suramin, CMC and poloxamer mixed the next day. 2 ml of each formulation was prepared. HPLC was used to measure the release profile. The results demonstrated that CMC influenced poloxamer micelle packing and associated release of suramin. FIG. 16 shows a release study of different concentrations of CMC with 20% w/v poloxamer. The results demonstrated that low CMC concentration slowed down release of suramin.

Figure 17:
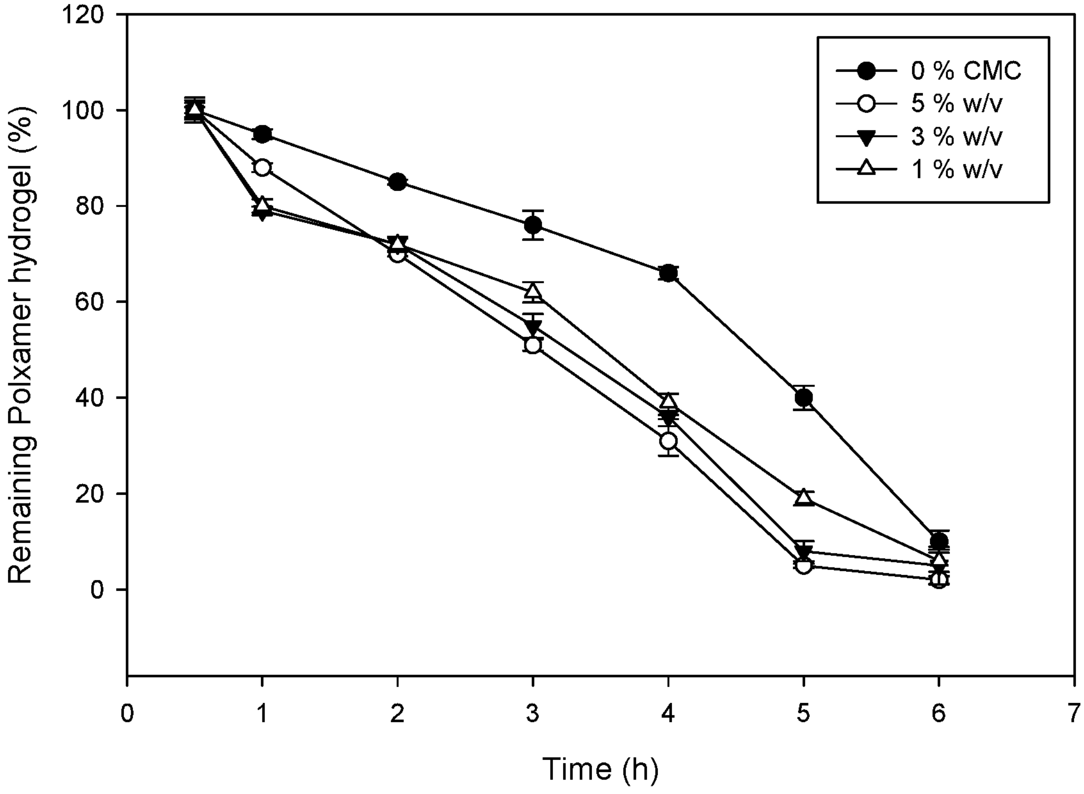
FIG. 17 shows degradation of carboxylmethyl chitosan/poloxamer hydrogels.
Figure 18:
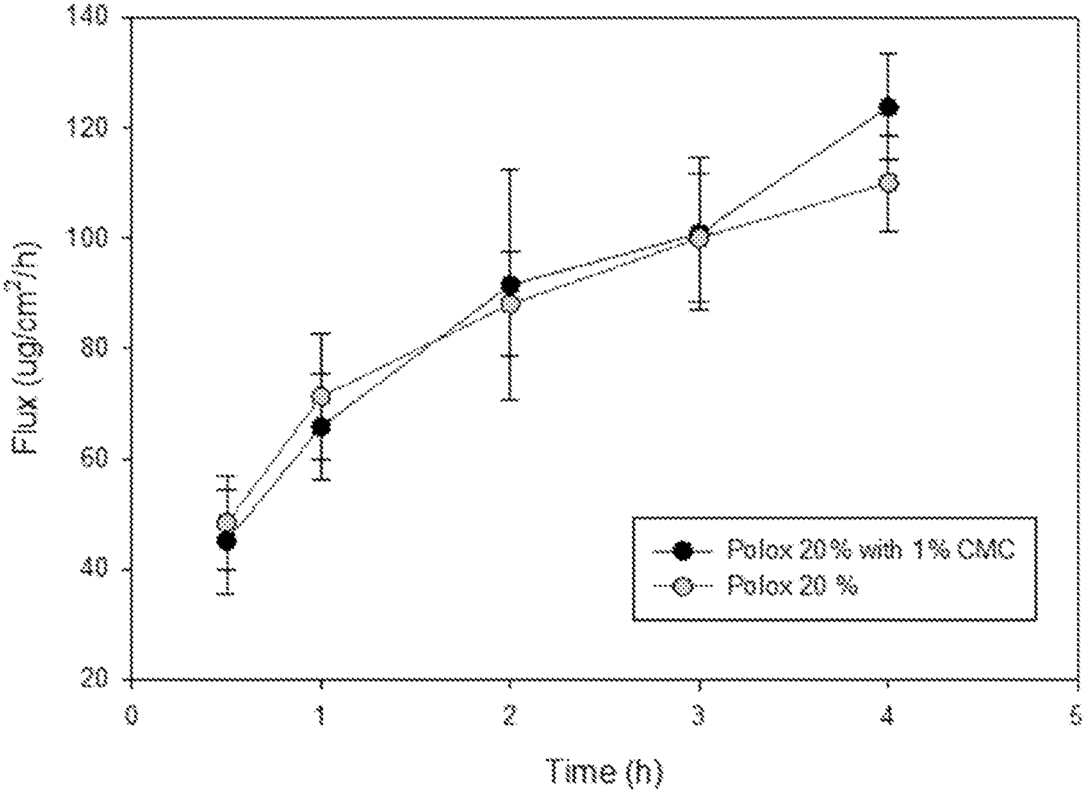
FIG. 18 shows suramin diffusion through Strep-M from suramin/carboxylmethyl chitosan/poloxamer hydrogels.

FIG. 17 shows degradation of a 20% poloxamer-CMC hydrogel at 37° C. The results show that higher CMC concentrations accelerate degradation of the hydrogel. FIG. 18 shows suramin diffusion through Strep-M from a poloxamer/CMC hydrogel. FIG. 19 snows cytotoxicity of hydrogels comprising CMC 2%+50, 100 or 200 μl GNP solution (10 mg/ml) and 100 μl suramin solution (10 mg/ml). Cell were incubated for 24 hours in a 6-well plate with 100,000 cell per well, seeded for 48 hours.

Example 5

This example describes diffusion or suramin through three-dimensional tissue models. Two different tissue models were used. EpiDerm (MatTek, Ashland, MA) is a ready-to-use, highly differentiated 3D tissue model of normal, human-derived epidermal keratinocytes (NHEK) cultured on specially prepared tissue culture inserts. EpiOral (MatTek) tissues are normal, human-derived oral epithelial cells. The cells have been cultured to form multilayered, highly differentiated models of the human buccal phenotypes. The following formulations were assayed on each tissue model:

| Formulations |
| --- |
| Suramin Free-solution |
| Carboxymethyl Chitosan Hydrogel |
| Poloxamer Hydrogel (20%) |
| Molecular mixture (Poloxamer 20% and 5% CMC w/w) |

Experiment conditions were a pH=7.4 and a temperature=35° C.

Figure 20:
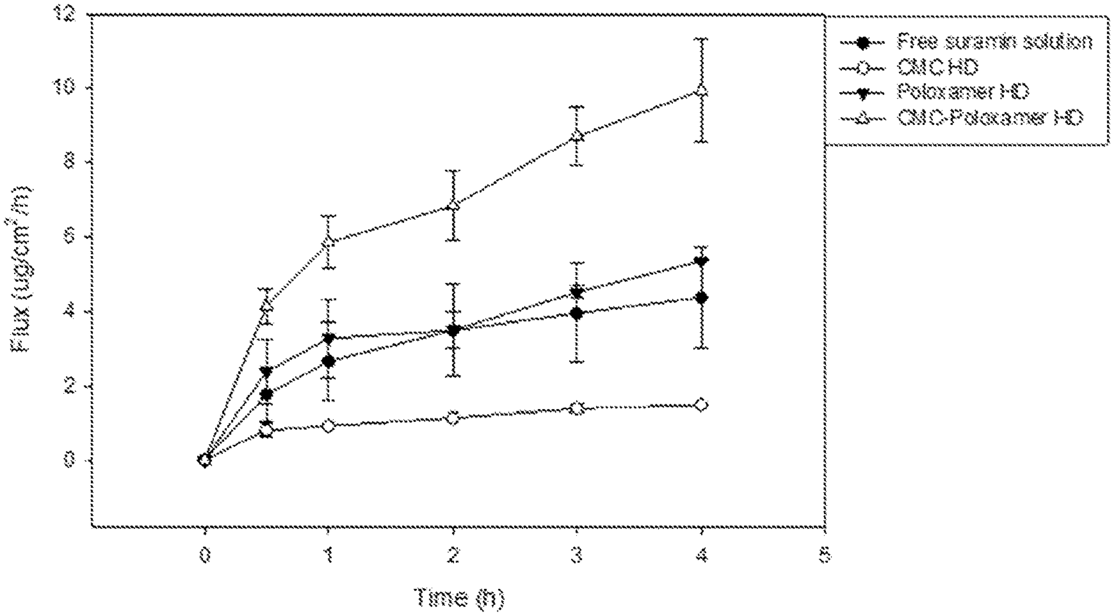
FIG. 20 shows suramin diffusion through a 3D cell model from various hydrogels.
Figure 21:
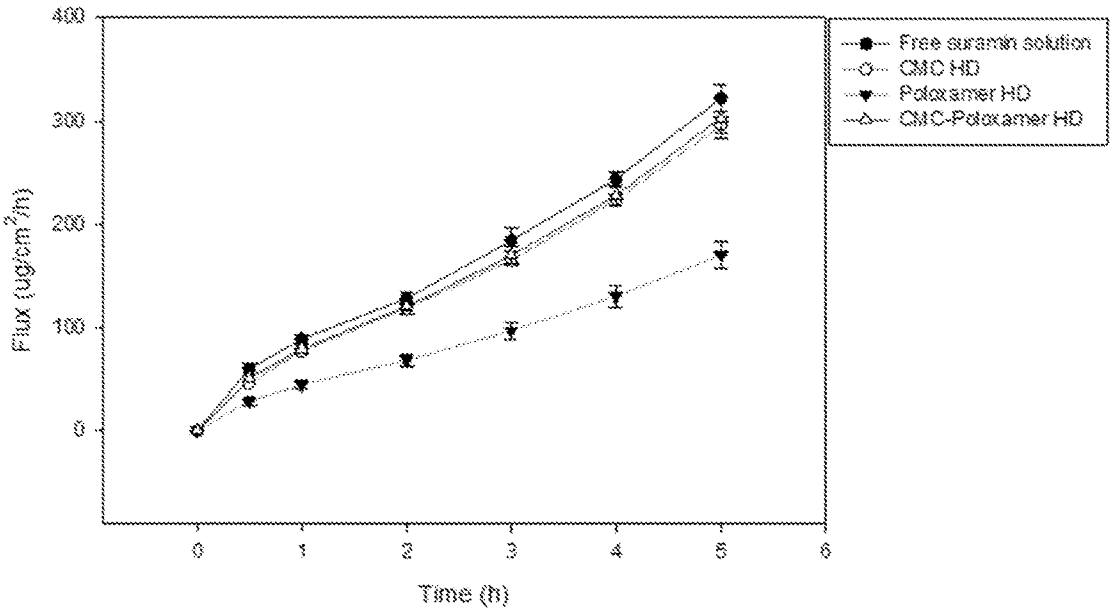
FIG. 21 shows suramin diffusion through a 3D cell model from various hydrogels.

Results are shown in FIG. 20 (Epiderm) and 21 (Epioral).

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A composition, comprising: suramin encapsulated in a crosslinked polymeric hydrogel comprising chitosan or carboxymethyl chitosan and poloxamer, wherein the composition is formulated for topical administration.

2. The composition of claim 1, wherein said crosslinked hydrogel is chemically physically, or oxidatively crosslinked.

3. The composition of claim 1, wherein said hydrogel further comprises a crosslinker.

4. The composition of claim 3, wherein said crosslinker is selected from the group consisting of glutaraldehyde, genipin, palladium cation, diisocyanate, and acrylic acid.

5. The composition of claim 1, wherein said chitosan is crosslinked in the presence of sodium bicarbonate.

6. The composition of claim 5, wherein said chitosan is crosslinked with sodium bicarbonate and genipin.

7. The composition of claim 6, wherein said sodium bicarbonate is present in said hydrogel at a concentration of 0.1 to 0.5M.

8. The composition of claim 7, wherein said sodium bicarbonate is present in said hydrogel at a concentration of 0.2 M.

9. The composition of claim 6, wherein said genipin is present in said hydrogel at a concentration of 1 to 3% by weight.

10. The composition of claim 1, wherein said chitosan is at a concentration of 0.5 to 5% w/v in said hydrogel.

11. A method of treating a wound in a subject, comprising: administering the composition of claim 1 to a subject with a wound under conditions such that said wound heals.

12. The method of claim 11, wherein said wound is selected from the group consisting of an acute wound and a chronic wound and ulcer.

13. The method of claim 11, wherein said subject has diabetes or mucositis.

14. The method of claim 11, further comprising administering an additional treatment for said wound.

15. The method of claim 14, wherein said additional treatment is selected from the group consisting of an antibiotic and a pain reliever.

16. A method of reducing the likelihood of developing a wound caused by radiation therapy, comprising: topically administering the composition of claim 1 to a subject at risk of developing a wound under conditions such that the likelihood of developing said wound is reduced, wherein said composition is administered prior to radiation therapy.

* * * * *